(12) United States Patent
Sato et al.

(10) Patent No.: US 6,395,786 B1
(45) Date of Patent: May 28, 2002

(54) SLEEP INDUCING AGENT

(75) Inventors: Fumie Sato, 2-1-901, Kugenumahigashi, Fujisawa-shi, Kanagawa 251-0026; Tohru Tanami, Tokyo; Kazuya Kameo, Tokyo; Kenji Yamada, Tokyo; Shigeru Okuyama, Tokyo; Naoya Ono, Tokyo, all of (JP)

(73) Assignees: Taisho Pharmaceutical Co., Ltd., Tokyo; Fumie Sato, Kanagawa, both of (JP)

( * ) Notice: Subject to any disclaimer, the term of this patent is extended or adjusted under 35 U.S.C. 154(b) by 0 days.

(21) Appl. No.: 09/701,332

(22) PCT Filed: May 25, 1999

(86) PCT No.: PCT/JP99/02723

§ 371 (c)(1),
(2), (4) Date: Nov. 27, 2000

(87) PCT Pub. No.: WO99/61029

PCT Pub. Date: Dec. 2, 1999

(30) Foreign Application Priority Data

May 25, 1998 (JP) ............................................. 10-142622

(51) Int. Cl.$^7$ ........................ A01N 37/08; A01N 53/00
(52) U.S. Cl. ...................... 514/573; 514/923; 554/214; 560/121; 562/523
(58) Field of Search ........................ 554/214; 560/121; 562/503; 514/573, 923

(56) References Cited

U.S. PATENT DOCUMENTS 5,599,838 A * 2/1997 Sato et al. .................. 514/530

FOREIGN PATENT DOCUMENTS

| EP | 0 652 211 A1 | 5/1995 | ......... C07C/405/00 |
|---|---|---|---|
| EP | 0 737 676 A1 | 10/1996 | ......... C07C/405/00 |
| JP | 07285929 | 10/1995 | ......... C07C/405/00 |

* cited by examiner

Primary Examiner—Deborah D. Carr
(74) Attorney, Agent, or Firm—Sughrue Mion, PLLC

(57) ABSTRACT

A sleep-inducing preparation which comprises as an effective ingredient a prostaglandin derivative represented by the formula:

wherein X is a halogen atom, Y is a group represented by $(CH_2)_m$, a cis-vinylene group or a phenylene group, Z is an ethylene group, a trans-vinylene group, $OCH_2$ or $S(O)_nCH_2$, $R^1$ is a $C_{3-10}$ cycloalkyl group, a $C_{3-10}$ cycloalkyl group substituted with $C_{1-4}$ alkyl group(s), a $C_{4-13}$ cycloalkylalkyl group, a $C_{5-10}$ alkyl group, a $C_{5-10}$ alkenyl group, a $C_{5-10}$ alkynyl group or a bridged cyclic hydrocarbon group, $R^2$ is a hydrogen atom, a $C_{1-10}$ alkyl group or a $C_{3-10}$ cycloalkyl group, m is an integer of 1 to 3, and n is 0, 1 or 2, a pharmaceutically acceptable salt thereof or a hydrate thereof.

6 Claims, 2 Drawing Sheets

SLEEP INDUCING AGENT

This application is a 371 of PCT/JP99/02123 filed May 25, 1994.

TECHNICAL FIELD

The present invention relates to a sleep-inducing preparation comprising a prostaglandin derivative as an effective ingredient.

BACKGROUND ART

Since prostaglandin (hereinafter referred to as "PG") exhibits various important physiological actions in a trace amount, the syntheses of the derivatives from natural PGs and the biological activities have been investigated with the intention of a practical use as medicines and have been reported in many literatures.

Particularly, PGs have been reported on the various central nervous actions and have been clarified as to the intracerebral content, biosynthesis, metabolic pathway, their intracerebral localizations and changes with growth or aging, and there has been taken an interest in the relation of PGs with sleep and wake. Among them, $PGD_2$ has been known as an intracerebral humoral factor which controls the occurrence or maintenance of sleep, and it was made clear that the sleep induced by $PGD_2$ in monkeys is undistinguished from the spontaneous natural sleep in brain wave or behavior (Proc. Natl. Acad. Sci. USA, vol. 85, pp. 4082–4086 (1988)), therefore this compound is expected as a compound having a novel sleep-inducing action.

However, $PGD_2$ derivatives including $PGD_2$ are presently unpractical due to the problems concerning the effect and the stability as a drug.

DISCLOSURE OF THE INVENTION

As a result of the extensive studies, the present inventors have found that the prostaglandin derivatives having a triple bond between the 13- and 14-position represented by the following formula (I) have a characteristic sleep-inducing action, and thereby the present invention has been accomplished.

That is, the present invention is directed to a sleep-inducing preparation which comprises as an effective ingredient a prostaglandin derivative represented by Formula (I):

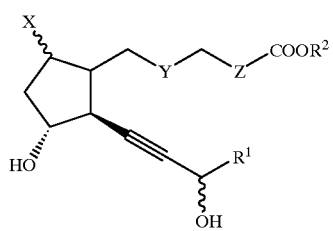

(I)

wherein X is a halogen atom, Y is a group represented by $(CH_2)_m$, a cis-vinylene group or a phenylene group, Z is an ethylene group, a trans-vinylene group, $OCH_2$ or $S(O)_nCH_2$, $R^1$ is a $C_{3-10}$ cycloalkyl group, a $C_{3-10}$ cycloalkyl group substituted with $C_{1-4}$ alkyl group(s), a $C_{4-13}$ cycloalkylalkyl group, a $C_{5-10}$ alkyl group, a $C_{5-10}$ alkenyl group, a $C_{5-10}$ alkynyl group or a bridged cyclic hydrocarbon group, $R^2$ is a hydrogen atom, a $C_{1-10}$ alkyl group or a $C_{3-10}$ cycloalkyl group, m is an integer of 1 to 3, and n is 0, 1 or 2, or a pharmaceutically acceptable salt thereof.

Further, the present invention is directed to a sleep-inducing preparation which comprises as an effective ingredient a prostaglandin derivative represented by Formula (I) wherein X is a chlorine atom or a bromine atom, Y is a group represented by $(CH_2)_m$ or a cis-vinylene group, Z is an ethylene group, a trans-vinylene group, $OCH_2$ or $S(O)_nCH_2$, $R^1$ is a $C_{3-10}$ cycloalkyl group or a $C_{4-13}$ cycloalkylalkyl group, $R^2$ is a hydrogen atom or a $C_{1-10}$ alkyl group, m is an integer of 1 to 3, and n is 0, 1 or 2, or a pharmaceutically acceptable salt thereof.

Furthermore, the present invention is directed to a sleep-inducing preparation which comprises as an effective ingredient a prostaglandin derivative represented by Formula (I) wherein X is a chlorine atom or a bromine atom, Y is a group represented by $(CH_2)_m$ or a cis-vinylene group, Z is $OCH_2$, $R^1$ is a $C_{3-10}$ cycloalkyl group or a $C_{4-13}$ cycloalkylalkyl group, $R^2$ is a hydrogen atom or a $C_{1-10}$ alkyl group, and m is an integer of 1 to 3, or a pharmaceutically acceptable salt thereof.

Still furthermore, the present invention is directed to a sleep-inducing preparation which comprises as an effective ingredient a prostaglandin derivative represented by Formula (I) wherein X is a chlorine atom or a bromine atom, Y is a group represented by $(CH_2)_m$ or a cis-vinylene group, Z is $SCH_2$, $R^1$ is a $C_{3-10}$ cycloalkyl group or a $C_{4-13}$ cycloalkylalkyl group, $R^2$ is a hydrogen atom or a $C_{1-10}$ alkyl group, and m is an integer of 1 to 3, or a pharmaceutically acceptable salt thereof.

Still furthermore, the present invention is directed to a sleep-inducing preparation which comprises as an effective ingredient a prostaglandin derivative represented by Formula (I) wherein Y is a group represented by $(CH_2)_m$, Z is $SCH_2$, $R^1$ is a $C_{3-10}$ cycloalkyl group, $R^2$ is a hydrogen atom or a $C_{1-10}$ alkyl group, and m is an integer of 1 to 3, or a pharmaceutically acceptable salt thereof.

Still furthermore, the present invention is directed to the above-mentioned prostaglandin derivative or the pharmaceutically acceptable salt for use as an ingredient for sleep-inducing preparation.

Still furthermore, the present invention is directed to a method for sleep-inducing comprising administering a pharmaceutically effective amount of the above-mentioned prostaglandin derivative or the pharmaceutically acceptable salt to a human.

In the present invention, the halogen atom refers to a fluorine atom, a chlorine atom, a bromine atom or an iodine atom.

Examples of the $C_{3-10}$ cycloalkyl group are a cyclopropyl group, a cyclobutyl group, a cyclopentyl group, a cyclohexyl group and a cycloheptyl group.

Examples of the $C_{3-10}$ cycloalkyl group substituted with $C_{1-4}$ alkyl group(s) are a methylcyclopropyl group, a methylcyclohexyl group and an ethylcyclohexyl group.

Examples of the $C_{4-13}$ cycloalkylalkyl group are a cyclopropylmethyl group, a cyclobutylmethyl group, a cyclopentylmethyl group, a cyclopentylethyl group, a cyclohexylmethyl group, a cyclohexylethyl group and a cycloheptylmethyl group.

The $C_{5-10}$ alkyl group refers to a straight or branched alkyl group, and examples thereof are a pentyl group, a hexyl group, a heptyl group, an octyl group, a 1-methylpentyl group, a 2-methylpentyl group, a 1-methylhexyl group, a 2-methylhexyl group, a 2,4-dimethylpentyl group, a 2-ethylpentyl group, a 2-methylheptyl group, a 2-ethylhexyl group, a 2-propylpentyl group, a 2-propylhexyl group and a 2,6-dimethylheptyl group.

The $C_{5-10}$ alkenyl group refers to a straight or branched alkenyl group, and examples thereof are a 3-pentenyl group, a 4-hexenyl group, a 5-heptenyl group, a 4-methyl-3-pentenyl group, a 2,4-dimethylpentenyl group, a 6-methyl-5-heptenyl group and a 2,6-dimethyl-5-heptenyl group.

The $C_{5-10}$ alkynyl group refers to a straight or branched alkynyl group, and examples thereof are a 3-pentynyl group, a 3-hexynyl group, a 4-hexynyl group, a 1-methylpent-3-ynyl group, a 2-methylpent-3-ynyl group, a 1-methylhex-3-ynyl group and a 2-methylhex-3-ynyl group.

Examples of the bridged cyclic hydrocarbon group are a bornyl group, a norbornyl group, an adamantyl group, a pinanyl group, a thujyl group, a caryl group and a camphanyl group.

The $C_{1-10}$ alkyl group for $R^2$ refers to a straight or branched alkyl group, and examples thereof are a methyl group, an ethyl group, a propyl group, an isopropyl group, a butyl group, an isobutyl group, a tert-butyl group, a pentyl group, an isopentyl group, a 2-ethylpropyl group, a hexyl group, an isohexyl group, a 1-ethylbutyl group, a heptyl group, an isoheptyl group, an octyl group, a nonyl group and a decyl group.

Examples of the pharmaceutically acceptable salt are salts with alkali metal (e.g. sodium or potassium), alkali earth metal (e.g. calcium or magnesium), ammonia, methylamine, dimethylamine, cyclopentylamine, benzylamine, piperidine, monoethanolamine, diethanolamine, monomethylmonoethanolamine, tromethamine, lysine, a tetraalkyl ammonium and tris(hydroxymethyl)aminomethane.

According to the sleep-inducing preparation of the present invention, in view of the sleep-inducing effect, Y is preferably an ethylene group or cis-vinylene group, Z is preferably $OCH_2$ or $SCH_2$, and $R^1$ is preferably a cycloalkyl group in Formula (I) of the prostaglandin derivatives as the effective ingredient.

Some of the compounds of Formula (I), according to the present invention, are known in WO94/02457, WO94/08959, Japanese Patent Kokai Hei-6-192218, Japanese Patent Kokai Hei-7-242622, Japanese Patent Kokai Hei-7-242623, Japanese Patent Kokai Hei-7-233144, Japanese Patent Kokal Hei-7-285929, Japanese Patent Kokai Hei-8-208599, Japanese Patent Kokal Hei-7-233143, Japanese Patent Kokal Hei-9-286775, Japanese Patent Kokai Sho-58-8059, Japanese Patent Kohyo Sho-60-501813 and Japanese Patent Kohyo Sho-60-500787.

On the other hand, the compounds wherein Z is $S(O)CH_2$ and $S(O)_2CH_2$ can be prepared by a reaction of the compounds wherein Z is $SCH_2$ using an oxidant such as sodium metaperiodide in a solvent such as methanol.

According to the present invention, representative compounds of Formula (I) are described as follows:

TABLE 1

(I)

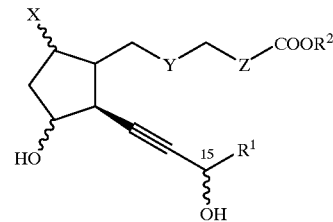

| Compound No. | X | Y | Z | $R^1$ | $R^2$ | 8-position | 15-position |
|---|---|---|---|---|---|---|---|
| Compound 1 | β-Cl | CH=CH | $OCH_2$ | cyclohexyl | tert-butyl | α | α |
| Compound 2 | β-Cl | CH=CH | $OCH_2$ | cyclohexyl | methyl | α | α |
| Compound 3 | β-Cl | CH=CH | $OCH_2$ | cyclohexyl | methyl | α | β |
| Compound 4 | β-Cl | CH=CH | $OCH_2$ | cyclohexyl | hydrogen | α | α |
| Compound 5 | β-Cl | CH=CH | $OCH_2$ | cyclohexyl | hydrogen | α | β |
| Compound 6 | β-Cl | CH=CH | $OCH_2$ | cyclohexyl | hydrogen | α | α |
| Compound 7 | β-Br | CH=CH | $OCH_2$ | cyclohexyl | hydrogen | α | α |
| Compound 8 | β-Br | CH=CH | $OCH_2$ | cyclohexyl | hydrogen | β | α |
| Compound 9 | F | CH=CH | $OCH_2$ | cyclohexyl | hydrogen | α | α |
| Compound 10 | β-Br | CH=CH | $OCH_2$ | cyclopentyl | hydrogen | α | α |
| Compound 11 | β-Br | CH=CH | $OCH_2$ | cycloheptyl | hydrogen | α | α |
| Compound 12 | β-Br | CH=CH | $OCH_2$ | cyclopentylmethyl | hydrogen | α | α |
| Compound 13 | β-Br | CH=CH | $OCH_2$ | cyclohexylmethyl | hydrogen | α | α |
| Compound 14 | β-Cl | CH=CH | $SCH_2$ | cyclohexyl | tert-butyl | α | α |
| Compound 15 | β-Cl | CH=CH | $SCH_2$ | cyclohexyl | hydrogen | α | α |
| Compound 16 | β-Cl | $CH_2CH_2$ | $OCH_2$ | cyclohexyl | tert-butyl | α | α |
| Compound 17 | β-Cl | $CH_2CH_2$ | $OCH_2$ | cyclohexyl | methyl | α | α |
| Compound 18 | β-Cl | $CH_2CH_2$ | $OCH_2$ | cyclohexyl | methyl | α | β |
| Compound 19 | β-Cl | $CH_2CH_2$ | $OCH_2$ | cyclohexyl | hydrogen | α | α |
| Compound 20 | β-Cl | $CH_2CH_2$ | $OCH_2$ | cyclohexyl | hydrogen | α | β |
| Compound 21 | β-Cl | $CH_2CH_2$ | $OCH_2$ | cyclopentyl | hydrogen | α | α |
| Compound 22 | β-Cl | $CH_2CH_2$ | $OCH_2$ | cycloheptyl | hydrogen | α | α |
| Compound 23 | β-Cl | $CH_2CH_2$ | $OCH_2$ | cyclopentylmethyl | hydrogen | α | α |
| Compound 24 | β-Cl | $CH_2CH_2$ | $OCH_2$ | cyclohexylmethyl | hydrogen | α | α |
| Compound 25 | α-Cl | $CH_2CH_2$ | $OCH_2$ | cyclohexyl | hydrogen | β | α |
| Compound 26 | β-Br | $CH_2CH_2$ | $OCH_2$ | cyclohexyl | hydrogen | α | α |
| Compound 27 | α-Br | $CH_2CH_2$ | $OCH_2$ | cyclohexyl | hydrogen | α | α |
| Compound 28 | F | $CH_2CH_2$ | $OCH_2$ | cyclohexyl | hydrogen | α | α |
| Compound 29 | β-Cl | $CH_2CH_2$ | $SCH_2$ | cyclohexyl | tert-butyl | α | α |
| Compound 30 | β-Cl | $CH_2CH_2$ | $SCH_2$ | cyclohexyl | methyl | α | α |
| Compound 31 | β-Cl | $CH_2CH_2$ | $SCH_2$ | cyclohexyl | methyl | α | β |
| Compound 32 | β-Cl | $CH_2CH_2$ | $SCH_2$ | cyclohexyl | hydrogen | α | α |

TABLE 1-continued

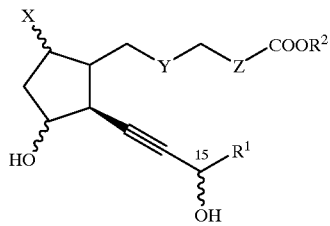

(I)

| Compound No. | X | Y | Z | R¹ | R² | 8-position | 15-position |
|---|---|---|---|---|---|---|---|
| Compound 33 | β-Cl | $CH_2CH_2$ | $SCH_2$ | cyclohexyl | hydrogen | β | α |
| Compound 34 | β-Cl | $CH_2CH_2$ | $SCH_2$ | cyclohexyl | hydrogen | α | β |
| Compound 35 | β-Cl | $CH_2CH_2$ | $SCH_2$ | cyclopentyl | hydrogen | α | α |
| Compound 36 | β-Cl | $CH_2CH_2$ | $SCH_2$ | cyclopentylmethyl | hydrogen | α | α |
| Compound 37 | β-Cl | $CH_2CH_2$ | $SCH_2$ | cyclohexylmethyl | hydrogen | α | α |
| Compound 38 | α-Cl | $CH_2CH_2$ | $SCH_2$ | cyclohexyl | hydrogen | α | α |
| Compound 39 | β-Br | $CH_2CH_2$ | $SCH_2$ | cyclohexyl | hydrogen | α | α |
| Compound 40 | α-Br | $CH_2CH_2$ | $SCH_2$ | cyclohexyl | hydrogen | α | α |
| Compound 41 | F | $CH_2CH_2$ | $SCH_2$ | cyclohexyl | hydrogen | α | α |
| Compound 42 | β-Cl | $CH_2CH_2$ | $OCH_2$ | 2-methyl-1-hexyl | hydrogen | α | α |
| Compound 43 | β-Cl | $CH_2CH_2$ | $SCH_2$ | 2-methyl-1-hexyl | hydrogen | α | α |
| Compound 44 | β-Cl | $CH_2CH_2$ | $OCH_2$ | 2,6-dimethyl-5-heptenyl | hydrogen | α | α |
| Compound 45 | β-Cl | $CH_2CH_2$ | $SCH_2$ | 2,6-dimethyl-5-heptenyl | hydrogen | α | α |
| Compound 46 | β-Cl | o-interphenylene | $OCH_2$ | cyclohexyl | hydrogen | α | α |
| Compound 47 | β-Cl | m-interphenylene | $OCH_2$ | cyclohexyl | hydrogen | α | α |
| Compound 48 | β-Cl | p-interphenylene | $OCH_2$ | cyclohexyl | hydrogen | α | α |
| Compound 49 | β-Cl | o-interphenylene | $SCH_2$ | cyclohexyl | hydrogen | α | α |
| Compound 50 | β-Cl | m-interphenylene | $SCH_2$ | cyclohexyl | hydrogen | α | α |
| Compound 51 | β-Cl | p-interphenylene | $SCH_2$ | cyclohexyl | hydrogen | α | α |
| Compound 52 | β-Cl | $CH_2CH_2$ | $CH_2CH_2$ | cyclohexyl | methyl | α | α |
| Compound 53 | β-Cl | $CH_2CH_2$ | $CH_2CH_2$ | cyclohexyl | hydrogen | α | α |
| Compound 54 | β-Cl | $CH_2$ | $CH_2CH_2$ | cyclohexyl | hydrogen | α | α |
| Compound 55 | β-Cl | $CH_2CH_2$ | $CH_2CH_2$ | cyclopentyl | hydrogen | α | α |
| Compound 56 | β-Cl | $CH_2CH_2$ | $CH_2CH_2$ | cycloheptyl | hydrogen | α | α |
| Compound 57 | β-Cl | $CH_2CH_2$ | $CH_2CH_2$ | cyclopentylmethyl | methyl | α | α |
| Compound 58 | β-Cl | $CH_2CH_2$ | $CH_2CH_2$ | cyclopentylmethyl | hydrogen | α | α |
| Compound 59 | β-Cl | $CH_2CH_2$ | $CH_2CH_2$ | cyclohexylmethyl | methyl | α | α |
| Compound 60 | β-Cl | $CH_2CH_2$ | $CH_2CH_2$ | cyclohexylmethyl | hydrogen | α | α |
| Compound 61 | β-Cl | $CH_2CH_2$ | $CH_2CH_2$ | 2-methyl-1-hexyl | methyl | α | α |
| Compound 62 | β-Cl | $CH_2CH_2$ | $CH_2CH_2$ | 2-methyl-1-hexyl | hydrogen | α | α |
| Compound 63 | β-Cl | $CH_2CH_2$ | $CH_2CH_2$ | 2,6-dimethyl-5-heptenyl | methyl | α | α |
| Compound 64 | β-Cl | $CH_2CH_2$ | $CH_2CH_2$ | 2,6-dimethyl-5-heptenyl | hydrogen | α | α |
| Compound 65 | β-Cl | $CH_2CH_2$ | $CH_2CH_2$ | 1-methyl-3-hexynyl | methyl | α | α |
| Compound 66 | β-Cl | $CH_2CH_2$ | $CH_2CH_2$ | 1-methyl-3-hexynyl | hydrogen | α | α |
| Compound 67 | β-Cl | $CH_2CH_2$ | CH=CH | cyclohexyl | tert-butyl | α | α |
| Compound 68 | β-Cl | $CH_2CH_2$ | CH=CH | cyclohexyl | Isopropyl | α | α |
| Compound 69 | β-Cl | $CH_2CH_2$ | CH=CH | cyclohexyl | methyl | α | α |
| Compound 70 | β-Cl | $CH_2CH_2CH_2$ | CH=CH | cyclohexyl | methyl | α | α |
| Compound 71 | β-Cl | $CH_2CH_2$ | CH=CH | cyclohexyl | hydrogen | α | α |
| Compound 72 | β-Cl | $CH_2CH_2CH_2$ | CH=CH | cyclohexyl | hydrogen | α | α |
| Compound 73 | β-Cl | $CH_2CH_2$ | CH=CH | cyclopentyl | methyl | α | α |
| Compound 74 | β-Cl | $CH_2CH_2$ | CH=CH | cyclopentyl | hydrogen | α | α |
| Compound 75 | β-Cl | $CH_2CH_2$ | CH=CH | cycloheptyl | methyl | α | α |
| Compound 76 | β-Cl | $CH_2CH_2$ | CH=CH | cycloheptyl | hydrogen | α | α |
| Compound 77 | β-Cl | $CH_2CH_2$ | CH=CH | cyclopentylmethyl | methyl | α | α |
| Compound 78 | β-Cl | $CH_2CH_2$ | CH=CH | cyclopentylmethyl | hydrogen | α | α |
| Compound 79 | β-Cl | $CH_2CH_2$ | CH=CH | cyclohexylmethyl | methyl | α | α |
| Compound 80 | β-Cl | $CH_2CH_2$ | CH=CH | cyclohexylmethyl | hydrogen | α | α |
| Compound 81 | β-Cl | $CH_2CH_2$ | CH=CH | 2-methyl-1-hexyl | methyl | α | α |
| Compound 82 | β-Cl | $CH_2CH_2$ | CH=CH | 2-methyl-1-hexyl | hydrogen | α | α |
| Compound 83 | β-Cl | $CH_2CH_2$ | CH=CH | 2,6-dimethyl-5-heptenyl | methyl | α | α |
| Compound 84 | β-Cl | $CH_2CH_2$ | CH=CH | 2,6-dimethyl-5-heptenyl | hydrogen | α | α |
| Compound 85 | β-Cl | $CH_2CH_2$ | CH=CH | 1-methyl-3-hexynyl | methyl | α | α |
| Compound 86 | β-Cl | $CH_2CH_2$ | CH=CH | 1-methyl-3-hexynyl | hydrogen | α | α |

The compounds in the present invention can be administered orally or parenterally such as intravenously or nasally. For example, they can be administered orally in the form such as tablets, dusting powders, granules, powders, capsules, solutions, emulsions or suspensions, each of which can be prepared according to conventional methods. As the dosage forms for intravenous administration, there are used aqueous or non-aqueous solutions, emulsions, suspensions or solid preparations to be dissolved in a solvent for injection immediately before use. Furthermore, nasal administration can be performed by spraying quantitatively a solution or a powder (hard capsules) containing the drug into the nasal cavity by use of a dedicated nasal dropper or sprayer. The compounds in the present invention can be formulated into the form of the inclusion compounds with α-, β- or γ-cyclodextrin, or methylated cyclodextrin. The dose is varied by the age, body weight, etc., but it generally is from 1 ng to 1 mg/day per adult.

INDUSTRIAL APPLICABILITY

The present invention makes it possible to provide a sleep-inducing preparation which is sufficiently effective and remarkably stable.

BEST MODE FOR CARRYING OUT THE INVENTION

Figure 1:
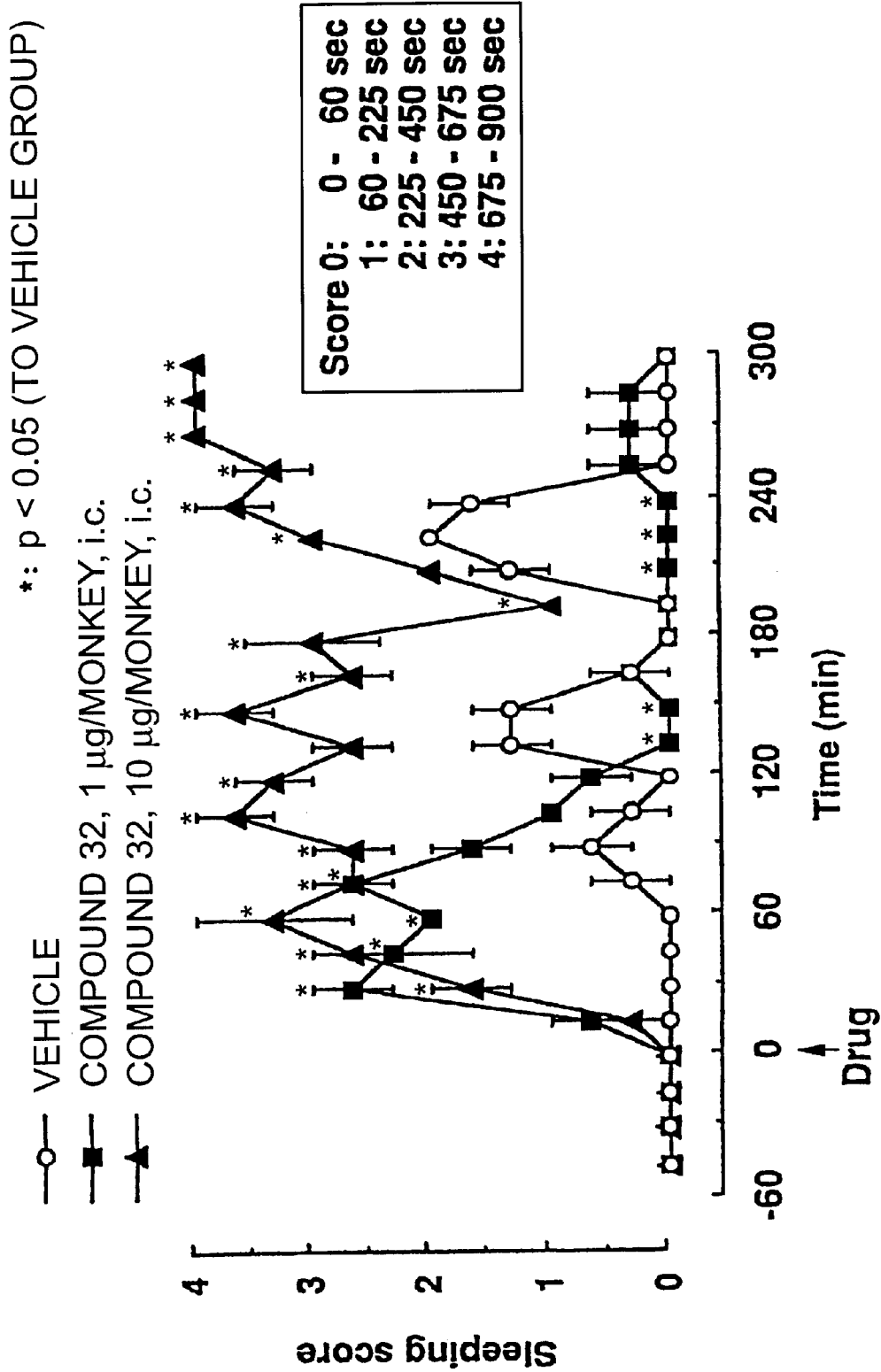
FIG. 1 is a drawing which shows a result of the sleep-inducing action by administration of Compound 32 according to Experiment 2.

The present invention is illustrated more particularly by the following examples and experiments.

EXAMPLE 1

With 1 mg of Compound 4 synthesized according to the method described in WO94/02457 was combined 30 mg of calcium carbonate (light), thereby a hard capsule preparation was obtained.

EXAMPLE 2

In 1 ml of an isotonic phosphate buffer (pH 7.4) was dissolved 10 mg of Compound 32 synthesized according to the method described in WO94/02267, thereby a nasal drop preparation was obtained.

EXAMPLE 3

In 1 ml of an isotonic phosphate buffer (pH 7.4) was dissolved 10 mg of Compound 23 synthesized according to the method described in WO94/08959, thereby a nasal drop preparation was obtained.

Experiment 1
[Sleep-inducing Test By Nasal Administration]
Method

Nine male rhesus monkeys weighing about 6 kg were divided into groups of 3 monkeys. In order to homogeneously spray drugs into the nasal cavity, calcium carbonate and sofalcone were used as carriers, and Test drug 1 (a hard capsule preparation containing 1 mg of Compound 4 and 30 mg of calcium carbonate (light)), Test drug 2 (a hard capsule preparation containing 1 mg of Compound 4 and 30 mg of calcium carbonate (heavy)) and Test drug 3(a hard capsule preparation containing 1 mg of Compound 4 and 30 mg of sofalcone) were nasally administered to 3 rhesus monkeys that were each fixed on the monkey chair without anesthesia using a nasal dropper (Jetlizer: manufactured by Unisiajex Co.), and the sleep-inducing action was observed (record by videotape) for an hour after the administration.

One week later, the behaviors in the control period of the same monkeys were observed.
Results In each case of the test drug, the sleep-inducing actin was definitely observed in 2 monkeys out of 3 (6 monkeys out of 9) in a period of from 5 to 15 minutes after the nasal administration, followed by drowsy stages.

On the other hand, no particular change was observed in the control group.

Experiment 2
[Sleep-inducing Test by Cisternal Administration]
Method

Three male rhesus monkeys weighing 3.6–4.4 kg were individually placed in cages, and the behaviors of the animals were recorded by videotape for an hour before administration of the drug and for 5 hours after administration of the drug. Compound 32 and prostaglandin $D_2$ methyl ester ($PGD_2$) were each dissolved in saline solution and sterilized through a Millipore filter. The drugs were infused cisternally to the monkeys anesthetized with isohalothane inhalation. The doses were 1 μg and 10 μg/0.1 ml/monkey. The same doses of the vehicle were infused cisternally to give a control group. The test was carried out according to the following test schedule.

Week 1: Group treated with vehicle
Week 2: Group treated with 1 μg of Compound 32/monkey
Week 3: Group treated with 10 μg of Compound 32/monkey
Week 4: Group treated with 10 μg of $PGD_2$/monkey To determine the sleep, the period for which the monkey closed both eyes was measured at intervals of 15 minutes by playing back the recorded videotape, and the results were scored according to the following scales.

| Score | Sleep time (15 minutes) |
|---|---|
| 0 | 0–60 seconds |
| 1 | 60–225 seconds |
| 2 | 225–450 seconds |
| 3 | 450–675 seconds |
| 4 | 675–900 seconds |

Results

Figure 2:
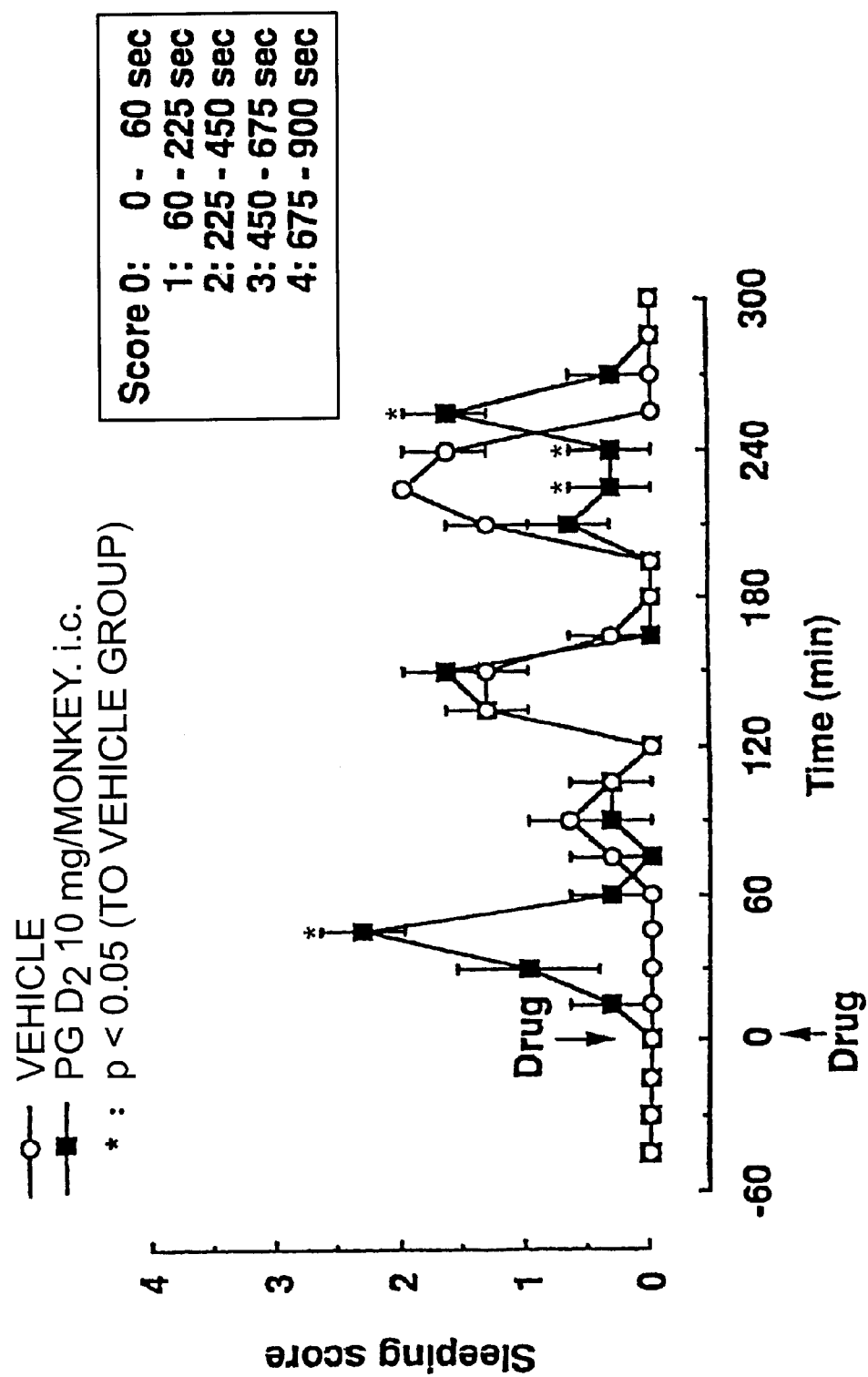
FIG. 2 is a drawing which shows a result of the sleep-inducing effect by administration of $PGD_2$ according to Experiment 2.

Ninety minutes, 135–150 minutes and 210–240 minutes after the administration, the vehicle-treated group was observed to take the weak sleep. In the group treated with 1 μg of Compound 32/monkey, the significant sleep action was observed 30–75 minutes after the administration when compared with the group treated with vehicle (FIG. 1). In the group treated with 10 μg of Compound 32/monkey, the significant sleep action was observed 45 minutes to 5 hours after the administration when compared with the group treated with vehicle (FIG. 1). The transient sleep action was observed in the group treated with 10 μg of $PGD_2$/monkey 45 minutes after the administration (FIG. 2).

Experiment 3
[Sleep-inducing Action By Cisternal Administration]

Brain wave was recorded according to the method described in the literature (H. ONOE, Proc. Natl. Acad. Sci., 1988, Vol. 185, p.4082).
Method Four male crab-eating monkeys weighing 3.0 kg–4.7 kg were used. For a chronic implantation of electrodes, surgical operation was aseptically performed under pentobarbital anesthesia, stainless steel screw electrodes were placed on the cerebral cortex and the occipital lobe, and stainless electrodes for electromyogram were placed on the cervical muscles, followed by soldering a lead of a telemetory system transmitter (TL10M3-D70-EEE, Data Sciences, Inc.). The transmitter was subcutaneously implanted into the posterior cervix. After the operation, the operative wound healed completely, and brain wave became stable, then the animals served for the test.

The cerebrospinal fluid was identified by insertion of a spiral needle into the cerebellomedullary cistern from the occipital region under sevoflurane-inhalation anesthesia, after which the test drug (isotonic sodium chloride solution of Compound 32 sterilized through a Millipore filter) was cerebellomedullary-cisternally administered in the amount of 10 μg/0.1 ml/monkey.

Brain wave (EEG) was continuously recorded by a data recorder using a telemetry system (UA-10, Data Sciences, Inc.) for 4 hours after the administration of the test substance, and the behaviors were observed by a video recording system. The changes of sleep-wake stages (wake, non-REM sleep and REM sleep) with time were observed by the changes of brain wave, electromyogram and behavior. And the wake, non-REM sleep, REM sleep times, and the frequency of REM sleep were determined in a period of from 20 minutes to 240 minutes after the administration of the test substance, and results are shown in Table 2.

TABLE 2

|  | Time (sec.) | | | Frequency of REM sleep |
| --- | --- | --- | --- | --- |
|  | Wake | Non-REM sleep | REM sleep |  |
| Vehicle-treated Group | 185 ± 14 | 52 ± 12 | 2.9 ± 2.5 | 9.5 |
| Drug-treated Group | 119 ± 19 | 106 ± 11 | 15.2 ± 11.2 | 25.0* |

*p < 0.05 (to vehicle-treated group)

What is claimed is:

1. A sleep-inducing preparation which comprises as an effective ingredient a prostaglandin derivative represented by Formula (I):

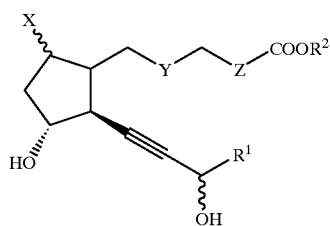

(I)

wherein X is a halogen atom, Y is a group represented by $(CH_2)_m$, a cis-vinylene group or a phenylene group, Z is an ethylene group, a trans-vinylene group, $OCH_2$ or $S(O)_nCH_2$, $R^1$ is a $C_{3-10}$ cycloalkyl group, a $C_{3-10}$ cycloalkyl group substituted with $C_{1-4}$ alkyl group(s), a $C_{4-13}$ cycloalkylalkyl group, a $C_{5-10}$ alkyl group, a $C_{5-10}$ alkenyl group, a $C_{5-10}$ alkynyl group or a bridged cyclic hydrocarbon group, $R^2$ is a hydrogen atom, a $C_{1-10}$ alkyl group or a $C_{3-10}$ cycloalkyl group, m is an integer of 1 to 3, and n is 0, 1 or 2, or a pharmaceutically acceptable salt thereof.

2. The sleep-inducing preparation according to claim 1 which comprises as an effective ingredient the prostaglandin derivative represented by Formula (I) wherein X is a chlorine atom or a bromine atom, Y is a group represented by $(CH_2)_m$ or a cis-vinylene group, Z is an ethylene group, a trans-vinylene group, $OCH_2$ or $S(O)_nCH_2$, $R^1$ is a $C_{3-10}$ cycloalkyl group or a $C_{4-13}$ cycloalkylalkyl group, $R^2$ is a hydrogen atom or a $C_{1-10}$ alkyl group, m is an integer of 1 to 3, and n is 0, 1 or 2, or a pharmaceutically acceptable salt thereof.

3. The sleep-inducing preparation according to claim 2 which comprises as an effective ingredient the prostaglandin derivative represented by Formula (I) wherein Z is $OCH_2$, or the pharmaceutically acceptable salt thereof.

4. The sleep-inducing preparation according to claim 2 which comprises as an effective ingredient the prostaglandin derivative represented by Formula (I) wherein Z is $SCH_2$, or the pharmaceutically acceptable salt thereof.

5. The sleep-inducing preparation according to claim 2 which comprises as an effective ingredient the prostaglandin derivative represented by Formula (I) wherein Y is a group represented by $(CH_2)_m$, Z is $SCH_2$, $R^1$ is a $C_{3-10}$ cycloalkyl group, or the pharmaceutically acceptable salt thereof.

6. A method for sleep-inducing comprising administering a pharmaceutically effective amount of a prostaglandin derivative represented by Formula (I):

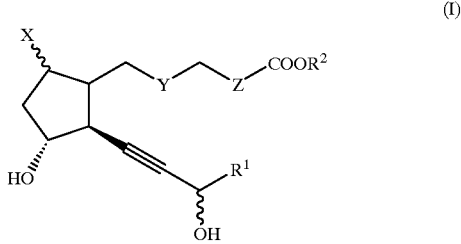

(I)

wherein X is a halogen atom, Y is a group represented by $(CH_2)_m$, a cis-vinylene group or a phenylene group, Z is an ethylene group, a trans-vinylene group, $OCH_2$ or $S(O)_nCH_2$, $R^1$ is a $C_{3-10}$ cycloalkyl group, a $C_{3-10}$ cycloalkyl group substituted with $C_{1-4}$ alkyl group(s), a $C_{4-13}$ cycloalkylalkyl group, a $C_{5-10}$ alkyl group, a $C_{5-10}$ alkenyl group; a $C_{5-10}$ alkynyl group or a bridged cyclic hydrocarbon group, $R^2$ is a hydrogen atom, a $C_{1-10}$ alkyl group or a $C_{3-10}$ cycloalkyl group, m is an integer of 1 to 3, and n is 0, 1 or 2, or a pharmaceutically acceptable salt thereof to a human.

* * * * *